United States Patent [19]

Cobb

[11] 4,179,580
[45] Dec. 18, 1979

[54] ORGANIC CHEMICAL REACTION
[75] Inventor: Raymond L. Cobb, Bartlesville, Okla.
[73] Assignee: Phillips Petroleum Company, Bartlesville, Okla.
[21] Appl. No.: 905,071
[22] Filed: May 11, 1978
[51] Int. Cl.$^2$ ............................................. C07C 3/52
[52] U.S. Cl. ........................... 546/349; 585/452; 585/453; 585/467; 585/516; 585/636; 260/346.11; 260/315; 260/319.1; 260/313.1; 549/86; 548/373
[58] Field of Search ............................ 260/668 B
[56] References Cited
U.S. PATENT DOCUMENTS

| | | | |
|---|---|---|---|
| 2,688,044 | 8/1954 | Pines et al. | 260/668 B |
| 2,849,508 | 8/1958 | Pines | 260/668 B |
| 2,994,725 | 8/1961 | Shaw | 260/668 B |
| 3,209,043 | 9/1965 | Cywinski et al. | 260/668 B |
| 3,291,847 | 12/1966 | Warner | 260/668 B |

OTHER PUBLICATIONS

Chem. Ab. 53, 21724h, 1959.

*Primary Examiner*—Veronica O'Keefe

[57] ABSTRACT

A process for increasing the reaction rate of condensation reactions which occur between non-conjugated non-aromatic olefinically unsaturated hydrocarbons and active hydrogen-containing organic compounds in the presence of alkali metal comprising carrying out the reaction in the presence of titanium metal.

23 Claims, No Drawings

ORGANIC CHEMICAL REACTION

This invention relates to an improvement in the alkali metal catalyzed condensation reaction of non-conjugated non-aromatic olefinically unsaturated hydrocarbons and organic compounds having suitably reactive hydrogen atoms.

Alkali metal catalyzed reactions between non-conjugated non-aromatic olefinically unsaturated hydrocarbons and active hydrogen-containing compounds are known in the art. The present invention is based upon the discovery that the rate of such reaction can be increased by employing a promoting amount of titanium.

Accordingly, an object of the present invention is to provide an improvement in the alkali metal catalyzed condensation of compounds containing an active hydrogen atom with non-conjugated non-aromatic olefinically unsaturated hydrocarbons.

Another object of the present invention is to provide an improved process for the side chain alkylation of a carbocyclic aromatic or heterocyclic aromatic compound having attached to a nuclear carbon atom a saturated carbon atom to which at least one hydrogen atom is bonded.

Still another object of the present invention is to improve the process for the alkylation of a hydrogen-containing saturated carbon atoms attached to a nuclear carbon atom of a carbocyclic aromatic compound.

A still further object of the present invention is to improve the process for the alkylation of the alkyl group of an alkyl-substituted carbocyclic aromatic compound with a non-conjugated olefinically unsaturated compound.

Other objects, aspects and advantages of the present invention will be apparent from the following disclosure.

In accordance with the present invention at least one non-conjugated non-aromatic olefinically unsaturated hydrocarbon is reacted with at least one active hydrogen organic compound in the presence of a catalytic amount of alkali metal promoted by titanium under conditions such that a condensation product of said at least one active hydrogen-containing organic compound and said at least one non-conjugated non-aromatic olefinically unsaturated hydrocarbon is formed.

While the molecular weight can vary widely, it is preferred that the non-conjugated non-aromatic olefinically unsaturated hydrocarbon contain 2 to 20 carbon atoms. Cyclic as well as acyclic non-conjugated non-aromatic olefinically unsaturated hydrocarbons are suitable. While olefins containing two or more non-conjugated carbon-to-carbon double bonds, i.e. 2.5-dimethyl-1.5-hexadiene, can be employed, monoolefins are presently preferred. Representative monoolefins include ethylene, propylene, 1-butene, 2-butene, isobutylene, 1-pentene, 2-pentene, 1-hexene, 2-hexene, 3-hexene, 2-decene, 1-heptene, 2-heptene, 2-octene, 4-nonene, 3-methyl-1-butene, 2-methyl-2-butene, 4-methyl-1-pentene, 1-eicosene, 3-tetradecene, 5-hexadecene, 6-methyl-4-heptadecene, and the like, including mixtures thereof. The lower monoolefins, such as ethylene or propylene, are the especially preferred non-conjugated olefin reactants.

The active hydrogen-containing organic compounds employed as reactants in accordance with the instant invention include monoolefinic hydrocarbons and carbocyclic aromatic or heterocyclic aromatic compounds having attached to an aromatic nuclear carbon atom a saturated carbon atom to which at least one hydrogen atom is bonded. The term saturated carbon as used herein is intended to indicate that each valence of the carbon atom is bonded to a different atom.

Examples of active hydrogen compounds of the monoolefinic hydrocarbon type include ethylene, propylene, 1-butene, 2-butene, isobutylene, 1-pentene, 2-pentene, 1-hexene, 2-hexene, 3-hexene, 1-heptene, 2-heptene, 3-heptene, the four normal octenes, the four normal nonenes, 3-methyl-1-butene, 2-methyl-2-butene, 3-methyl-1-pentene, 3-methyl-2-pentene, 4-methyl-1-pentene, 4-methyl-2-pentene, tetramethylethylene, 1-methylcyclohexene, 1-ethylcyclohexene, 1-(1-propyl)-cyclohexene, 1,2-dimethylcyclohexene, 1,4-dimethylcyclohexene, 1,3,5-trimethylcyclohexene, and the like, and mixtures thereof. Generally, it is preferred for the monoolefinic hydrocarbons to contain 2 to 20 carbon atoms.

It is to be noted that the term "aromatic" as used herein in connection to carbocyclic and heterocyclic is meant to include not only benzenes, naphthalenes, and derivatives thereof, but all compounds containing a stable ring or nucleus having aromatic character such as possessed by benzene.

Examples of suitable carbocyclic aromatic compounds include toluene, ethylbenzene, n-propylbenzene, isopropylbenzene, n-butylbenzene, sec-butylbenzene, isobutylbenzene, n-decylbenzene, 1,2,3,4-tetra-n-pentylbenzene, n-eicosylbenzene, 1-ethyl-4-n-octadecylnaphthalene, m-xylene, o-xylene, p-xylene, mesitylene, 1-methylnaphthalene, 1,2,4,5-tetramethylbenzene, 1,4-di-n-pentylnaphthalene, tetralin, indan, diphenylmethane, cyclopentylbenzene, cyclohexylbenzene, methylcyclohexylbenzene, and the like, and mixtures thereof. Generally the carbocyclic aromatic compounds will have 6 to 20 nuclear atoms, and a total of 7 to 100 carbon atoms. The especially preferred carbocyclic aromatic compounds are alkyl-substituted aromatic hydrocarbons having 1 to 4 alkyl substituents and containing 1 to 20 carbon atoms. Further, while the carbocyclic aromatic nucleus can have other substituents which are unreactive under the alkylation condition, it is preferred that the carbocyclic aromatic compound be strictly hydrocarbon.

Examples of suitable heterocyclic aromatic compounds include those having a pyridine, furan, thiophene, pyrrole, pyrazole, etc. nucleus having attached to an aromatic nuclear carbon atom a saturated carbon atom to which at least one hydrogen atom is bonded. Typical examples include picolines such as 2-methylpyridine, 3-methylpyridine, and 4-methylpyridine. Also included are those heterocyclic aromatic compounds which contain a carbocyclic ring as well as a heterocyclic ring. Examples of such compounds would include alkylated derivatives of compounds such as indole and carbazole. Generally, the heterocyclic aromatic will have 5 to 20 nuclear atoms and a total of 5 to 100 carbon atoms.

The reaction conditions employed in the instant invention can vary widely depending upon the particular non-conjugated non-aromatic olefinically unsaturated hydrocarbons and active hydrogen-containing reactants used, the desired products, and the desired yields. Generally the reaction temperature will be in the range of about 100° to about 350° C., preferably about 125° to about 250° C. Generally the pressure is mantained at a level sufficient to maintain the reactants in liquid phase. Typically the reaction would thus be conducted with the pressure in the range of about 250 to about 600 psig, preferably about 400 to about 500 psig, though higher pressures, e.g. as high as even 1200 psig, may be employed if desired, depending upon the reactants chosen and how they are charged and what reaction temperature is selected.

The reaction period can also vary widely depending upon the yield desired. Generally the reaction period will range from 1 hour to as much as 50 hours, or even longer. Because of the high production rates obtained with the use of the novel catalyst system, the reaction period will be shorter than that found necessary heretofore to obtain equivalent yields and conversions.

The process of this invention can be carried out with any suitable equipment, such as a steel or titanium autoclave or tubular reactor which provides for adequate mixing of the reactants. The reaction can be carried out in either a batch or a continuous fashion, with the reactants brought into contact in any order of addition. It may be desirable in some uses to carry out the reaction in a continuous manner, for example, by passing the reactants over or through a fixed bed of supported catalyst, with continuous or incremental addition of small amounts of the alkali metal catalyst components to the top of the bed with the feed to maintain catalyst activity and high production rate. In charging the reactants and in carrying out the reaction, care should be taken to exclude air or oxygen-containing gas and moisture which tends to adversely affect the reaction. This can be accomplished by purging the reactor with dry nitrogen or other dry, inert gas prior to charging it with the reactants and catalyst and by pressuring the reactants and catalyst into the reaction vessel with such gas.

The reactants can be dried and preheated if desired and introduced separately or as a mixture into the reaction zone. After the reaction is complete the reaction mixture can be cooled, gases and vapors vented therefrom, and the reaction mixture filtered to remove catalyst and support. The liquid reaction product can be fractionally distilled or otherwise separated to obtain the desired product. Unreacted reactants can be recovered and recycled to the reaction zone if desired. The catalyst and any metalated compounds present can be inactivated or decomposed, if desired, by adding to the reaction residue a polar (active hydrogen) compound, for example, water or an alcohol such as methanol or isopropanol.

The alkali metals, viz. lithium, sodium, potassium, rubidium, and cesium are not equally active as catalysts. Generally, the activity of the alkali metals increases with their atomic weight. The more plentiful sodium and potassium, and mixtures thereof, such as sodium-potassium alloys, are currently preferred. Since sodium generally requires higher reaction temperatures the presently especially preferred alkali metal is potassium or a sodium-potassium alloy.

The alkali metal can be employed in any suitable form. Preferably in order to maximize surface area the alkali metal is employed in a particulate, powdered, or finely divided form. In an especially preferred embodiment the alkali metal is in a colloidal or near colloidal form, e.g. having average particle size in the range of about 0.5 to 1000 millimicrons. The preferred sodium-potassium alloys are those which are typically liquid at room temperature, i.e. those having 40 to 90 weight percent potassium. The alloy containing 78 weight percent potassium is especially preferred because it is a eutectic.

Preferably the alkali metal is employed in conjunction with a support to increase surface area to provide for better contacting of the reactants. Examples of typical support materials include activated charcoal, granular coke, silicon, pumice, porcelain, quartz, steel turnings, copper shot, etc. An especially preferred support is soda ash. In a preferred embodiment of the instant invention the alkali metal in particulate, powdered, or finely divided form is mixed with a suitable support and the mixture heated above the melting point of the metal to aid dispersion. Preferably the alkali metal is used in a colloidal or near colloidal form, e.g. 0.5 to 1000 millimicrons as the high surface area of such particles promotes a higher reaction rate.

Preferably when soda ash (i.e. sodium carbonate) is employed as a support it is also used in a particulate or finely divided form, for example particles being in the range of about 20 to about 100 mesh (U.S. standard sieve).

The amount of alkali metal catalyst used in the reaction will be any amount sufficient to catalyze the desired reaction. The amount of alkali metal catalyst will generally be in the range of about 0.01 to about 1 gram atom per mole of the active hydrogen organic compound reactant. When a support is employed the amount of alkali metal on the support is generally in the range of about 0.5 to about 20 weight percent of the combined weight of alkali metal and support, preferably about 1 to about 11 weight percent.

The titanium promoter employed with alkali metal catalyst can be in any form that produces an increase in the reaction rate. For example, the titanium can be in the form of a finely divided powder, an alloy with other materials, i.e. cobalt, or as a reactor surface. The amount of added titanium promoter will be any amount that acts as a promoter, but will generally be in the range of from about 5 to about 200 weight percent of the alkali metal catalyst, preferably about 20 to about 130 weight percent.

The titanium promoter can be added to the reaction mixture in any manner that results in the promoting effect of the invention. The titanium powder or alloy can be mixed with the alkali metal and support when a supported catalyst is preformed or it can be charged directly to the reactor.

The molar ratio of active hydrogen organic compound to non-conjugated non-aromatic olefinically unsaturated hydrocarbon can vary widely, but will generally be in a range of about 0.1 to about 20, and will preferably be in the range of about 0.3 to about 2. While the non-conjugated non-aromatic olefinically unsaturated hydrocarbon can be used in amounts greater than the stoichiometric amount, it is preferable in most cases to operate with less than a stoichiometric amount of that reactant.

The reaction can generally be carried out with or without the addition of diluent. When the active hydrogen organic compound is used in excess with regard to the other reactant, it functions as a diluent. However, other diluents such as liquid paraffins, cycloparaffins, and aromatics can be employed using, for example, 10 to 200 volume percent of diluent, based on the volume of the active hydrogen organic compound. Of course the diluent must not be a material which will prohibit the formation of the desired reaction products. Thus preferably the diluent should be inert under the reaction conditions employed. Also it is preferable if the diluent has a boiling point that is significantly different from that of the reactants and product so as to allow more easy separation of those materials, by means such as fractional distillation. Specific examples of suitable diluents include n-pentane, n-hexane, isooctane, cyclohexane, naphthalene, decahydronaphthalene, white oils, etc.

The instant invention is particularly suitable for the side chain alkylation of alkyl-substituted carbocyclic aromatic compounds with monoolefins.

The instant invention and its advantages will be further illustrated by the following examples:

EXAMPLE I

Toluene was alkylated with propylene in a number of batch reactions. In each of these runs, the sodium carbonate support, alkali metal, toluene, and titanium powder (Alfa Chemical Co., 325 mesh) when used, were added under a nitrogen blanket to a 1-liter stainless steel autoclave equipped with a stirrer with an operating speed of 1800–2000 r.p.m. The alkali metal employed was a commercial NaK alloy containing 22 weight percent Na and 78 weight percent K. The reactor was closed and propylene was added to the reactor. The reactor was then heated to the operating temperature, usually 200° C., and the run was carried out at autogenous pressure. The reaction was terminated when the reactor pressure had dropped to about 300–400 psig and the reactor was cooled, vented, and opened. The reaction mixture was diluted with about an equal volume of pentane and filtered through a Filter aid. The filtrate was evaporated and then fractionally distilled under vacuum through a 15-inch (38 cm) column packed with glass helices. A sample of the original reaction product mixture and the distillation product were examined by gas-liquid chromatography (glc) to determine the composition of the reaction mixture and the conversion of toluene to the desired isobutylbenzene product. Titanium powder was present in runs 2 and 3, but not in runs 1 and 4. Run 4 was conducted after the completion of run 3 to determine any residual effect of the titanium powder. The reactants, conditions of reaction, and results are summarized in Table I.

TABLE I

|  | Run 1 | Run 2 | Run 3 | Run 4 |
|---|---|---|---|---|
| NaK Catalyst, g. | 4.9 | 3.3 | 3.6 | 3.9 |
| Titanium[a], g. | 0 | 3–4 | 1–2 | 0 |
| Support ($Na_2CO_3$), g. | 45 | 35 | 35 | 45 |
| Propylene, g. | 167 | 174 | 161 | 169 |
| Toluene, g. | 150 | 150 | 150 | 150 |
| Temp., °C. | 200° | 200° | 200° | 200° |
| Pressure, psig (MPa)[b] | 955(6.86) | 1030(7.1) | 1030(7.1) | 1015(7.0) |
| Time at 200° C. min | 390 | 320 | 335 | 258 |
| Toluene conversion, mole % | 87 | 90.1 | 88 | 96.4 |
| Isobutylbenzene Selectivity, % | 82.8 | 82.8 | 82.8 | 80.1 |
| Production rate, g./min | 0.359 | 0.431 | 0.436 | 0.5 |
| Distillation residue (heavies), g. | 4.17 | 2.47 | 3.10 | 2.31 |

[a]325 mesh powder.
[b]Maximum pressure developed during the run.

A comparison of runs 2 and 3 with run 1 shows that the presence of titanium powder in the alkylation reaction gave higher reaction rates and lower heavies levels than a similar reaction in the absence of titanium. The results of run 4 indicate that there is an unexpected residual effect of the titanium powder on the next reaction.

EXAMPLE II

Toluene was alkylated with propylene in two batch runs in a 1-liter titanium autoclave. In both of these runs, the sodium carbonate support, catalyst, toluene, and titanium powder (Alfa Chemical Co., 325 mesh), when used, were added under a nitrogen blanket to a 1-liter titanium autoclave equipped with a stirrer which was operated at 1200–1250 r.p.m. The reactor was sealed and about 120 g. of propylene was added. The reactor was then heated to 160° C., and propylene was added to the reactor at a rate sufficient to maintain the reactor pressure between about 450 to 500 psig (3.1 to 3.45 MPa). The reaction was terminated about 240 to 250 minutes after the reactor temperature reached 200° C. and the reactor was cooled, vented, and opened. The reaction product mixture was isolated and analyzed in a manner similar to that used in Example I. The reactants, conditions on reaction, and results are summarized in Table II.

TABLE II

|  | Run 5 | | Run 6 | |
|---|---|---|---|---|
| NaK Catalyst, g. |  | 6 |  | 5.1 |
| Titanium, g. |  | 0 |  | 5–6 |
| Support ($Na_2CO_3$), g. |  | 72 |  | 72 |
| Propylene, g. |  | 258 |  | 276 |
| Toluene, g. |  | 450 |  | 450 |
| Temp., °C. |  | 200 |  | 200 |
| Pressure, psig (MPa) | 450–500 | (3.1–3.45) | 450–500 | (3.1–3.45) |
| Time at 200° C. min. |  | 248 |  | 240 |
| Toluene conversion, mole % |  | 69.7 |  | 74.1 |
| Isobutylbenzene Selectivity, % |  | 85.3 |  | 85.3 |
| Production rate, g/min |  | 1.337 |  | 1.522 |
| Distillation residue (heavies),g. |  | 5.08 |  | 4.65 |

A comparison of runs 5 and 6 shows that the presence of titanium powder in a titanium reactor gave a higher toluene conversion, higher production rate, and lower heavies level in an alkylation reaction than a similar run in the absence of titanium powder.

EXAMPLE III

Toluene was alkylated with propylene in two batch runs to demonstrate the use of a titanium-cobalt alloy. In both of these runs, the sodium carbonate support, catalyst, toluene and the titanium-cobalt alloy (Alfa Chemical Co., 325 mesh), when used, were added under a nitrogen blanket to a 1-liter titanium autoclave equipped with a stirrer which was operated at ca. 800 r.p.m. The reactor was sealed, heated to 160° C., and about 35 g. of propylene was added to the reactor. The remainder of the propylene was added to the reactor at a rate sufficient to maintain the reactor pressure at around 500 psig (3.45 MPa). The reactions were terminated about 180 minutes after the reactor temperature had reached 190° C. and the products were isolated and analyzed in a manner similar to that described in Example I. The reactants, conditions of reaction, and results are summarized in Table III.

Table III

|  | Run 7 | Run 8 |
| --- | --- | --- |
| NaK Catalyst, g. | 5 | 4.8 |
| Ti-Co(a), g. | 0 | 3 |
| Support (Na$_2$CO$_3$), g. | 72 | 72 |
| Propylene, g. | 130 | 140 |
| Toluene, g | 400 | 400 |
| Temp., °C. | 190° | 190° |
| Pressure, psig (MPa) | 500 (3.45) | 500 (3.45) |
| Time at 190° C., min | 180 | 180 |
| Toluene conversion, mole % | 13.5 | 16.9 |
| Isobutylbenzene Selectivity, % | 87.7 | 87.3 |
| Production rate, g./min. | 0.28 | 0.406 |
| Distillation residue (heavies), g. | 0.44 | 0.82 |

(a)94/6 Weight ratio titanium-cobalt alloy (325 mesh).

A comparison of runs 7 and 8 shows that the presence of a titanium-cobalt alloy in the alkylation of toluene with propylene to produce isobutylbenzene results in an increase in the rate of reaction over a similar reaction in the absence of a titanium-cobalt alloy.

EXAMPLE IV

Toluene was alkylated with propylene in two batch runs to show the effect of the autoclave composition on the reaction rate. In each run, the sodium carbonate support, catalyst, and toluene were added under a nitrogen blanket to a 1-liter autoclave constructed of either stainless steel or titanium and equipped with a stirrer which was operated at 1900 to 2000 r.p.m. The reactor was sealed and propylene was added to the reactor. The reactor was then heated to 200° C. and the run was carried out at autogenous pressure. The reaction was terminated when the reactor pressure had dropped to about 300-450 psig, and the reactor was cooled, vented, and opened. The reaction product mixture was isolated and analyzed as described in Example I. The reactants, conditions of reaction, and results are summarized in Table IV.

Table IV

|  | Run 9 | Run 10 |
| --- | --- | --- |
| Reactor | Stainless Steel | Titanium |
| NaK Catalyst, g. | 4.2 | 3.9 |
| Support (Na$_2$CO$_3$), g. | 45 | 45 |
| Propylene, g. | 160 | 163 |
| Toluene, g. | 150 | 150 |
| Temp., °C. | 200° | 200° |
| Pressure, psig (MPa) | 950 (6.55) | 880 (6.07) |
| Time at 200° C. | 340 | 250 |
| Toluene conversion, Mole % | 82 | 95 |
| Isobutylbenzene Selectivity, % | 82.4 | 83.3 |
| Production rate, g./min. | 0.382 | 0.608 |

A comparison of runs 9 and 10 shows that the alkylation of toluene with propylene to yield isobutylbenzene proceeds at a higher rate and with a higher conversion in a titanium reactor than in a stainless steel reactor.

EXAMPLE V

Toluene was alkylated with propylene in two batch runs to show the effect of a titanium-cobalt alloy on the rate of reaction in the presence of butadiene, which is disclosed in U.S. Pat. No. 2,849,508 as a promoter for alkylation reactions. In each run, the sodium carbonate support, catalyst, toluene, and titanium-cobalt alloy (94 weight % titanium), when used, were charged under a nitrogen blanket to a 1-liter titanium autoclave equipped with a stirrer which was operated at 800 r.p.m. The reactor was sealed, heated to 160° C., and a small amount of butadiene in about 35 g. of propylene was added to the reactor. The remainder of the propylene was added to the reactor at a rate sufficient to maintain the reactor pressure at about 450-500 psig (3.1-2.45 MPa). The reaction was terminated 180 minutes after the first addition of propylene to the reactor. The reactor was cooled, vented, and opened and the reaction product mixture separated and analyzed as described in Example I. The reactants, conditions of reaction, and results are summarized in Table V.

Table V

|  | Run 11 | Run 12 |
| --- | --- | --- |
| NaK Catalyst, g. | 3.9 | 4 |
| Butadiene, g. | 1.36 | 1.27 |
| Ti-Co, g. | 0 | 6.1 |
| Support (Na$_2$CO$_3$), g. | 72 | 72 |
| Propylene, g. | 242 | 236 |
| Toluene, g. | 400 | 400 |
| Temp., °C. | 190° | 190° |
| Pressure, psig (MPa) | 450-500 | 450-500 |
| Time from first propylene addition, min. | 160 | 160 |
| Toluene conversion, mole % | 70.9 | 72.1 |
| Isobutylbenzene Selectivity, % | 85.6 | 85.8 |
| Production rate, g./min | 1.292 | 1.282 |

A comparison of runs 11 and 12 shows that a titanium-cobalt alloy does not increase the rate of reaction of the alkylation of toluene with propylene in the presence of small amounts of butadiene over a similar reaction in the absence of the titanium-cobalt alloy. Thus at least in this case there is no advantage to using the titanium metal promoter when a butadiene promoter is employed.

From the foregoing description and illustrative examples, one skilled in the art can easily ascertain the essential characteristics of this invention and without departing from the spirit and scope thereof, can make various changes and modifications of the invention to adapt it to various usages and conditions. Consequently, such changes and modifications should be viewed as being within the range of equivalence of the following claims.

What is claimed is:

1. A process comprising reacting at least one non-conjugated non-aromatic olefinically unsaturated hydrocarbon with at least one active hydrogen-containing organic compound selected from the group consisting of monoolefinic hydrocarbons and carbocyclic aromatic or heterocyclic aromatic compounds having attached to an aromatic nuclear carbon atom a saturated carbon atom to which at least one hydrogen atom is bonded, in the presence of a catalytic amount a catalyst system consisting essentially of alkali metal promoted by elemental titanium under conditions such that a condensation product of said at least one active hydrogen-containing organic compound and said at least one non-conjugated non-aromatic olefinically unsaturated hydrocarbon is formed.

2. A process according to claim 1 wherein the reaction temperature is in the range of about 100° to about 350° C. and the reaction pressure is in the range of about 250 psig to about 1200 psig.

3. A process according to claim 2 wherein about 0.01 to about 1 gram atom of alkali metal catalyst is employed per mole of said active hydrogen-containing compound.

4. A process according to claim 3 wherein the amount of titanium promoter is in the range of about 5 to about 200 weight percent of the weight of the alkali metal catalyst.

5. A process according to claim 4 wherein said alkali metal catalyst is employed in conjunction with a support and the amount of alkali metal on the support is in the range of about 0.5 to about 20 weight percent of the combined weight of the alkali metal and support.

6. A process according to claim 4 wherein each said active hydrogen-containing organic compound is selected from one or more monoolefinic hydrocarbons.

7. A process according to claim 6 wherein each said monoolefinic hydrocarbon has 2 to 20 carbon atoms.

8. A process according to claim 4 wherein each said active hydrogen-containing organic compound is selected from one or more heterocyclic aromatic compounds having attached to an aromatic nuclear carbon atom a saturated carbon atom to which at least one hydrogen is bonded.

9. A process according to claim 1 wherein each said active hydrogen-containing organic compound is selected from one or more carbocyclic aromatic compounds having attached to an aromatic nuclear carbon atom a saturated carbon atom to which at least one hydrogen is bonded.

10. A process according to claim 9 wherein each said carbocyclic aromatic compound has 6 to 20 nuclear atoms and a total of 7 to 100 carbon atoms.

11. A process according to claim 10 wherein each said carbocyclic aromatic compound is an alkyl-substituted aromatic having 1 to 4 alkyl substituents each containing 1 to 20 carbon atoms.

12. A process according to claim 11 wherein each said carbocyclic aromatic compound is a hydrocarbon.

13. A process according to claim 12 wherein the reaction temperature is in the range of about 100° to about 350° C. and the reaction pressure is in the range of about 250 psig to about 1200 psig, wherein about 0.01 to about 1 gram atom of alkali metal catalyst is employed per mole of said carbocyclic aromatic compound, and wherein the amount of titanium promoter is in the range of about 5 to about 200 weight percent of the weight of the alkali metal catalyst.

14. A process according to claim 13 wherein each said non-conjugated non-aromatic olefinically unsaturated hydrocarbon is selected from the group consisting of monoolefinic hydrocarbons having 2 to 20 carbon atoms.

15. A process according to claim 14 wherein each said monoolefinic hydrocarbon is selected from ethylene and propylene.

16. A process according to claim 14 wherein said alkali metal is selected from the group consisting of potassium, sodium, and potassium-sodium alloys.

17. A process according to claim 16 wherein alkali metal is employed with a sodium carbonate support.

18. A process according to claim 17 wherein said titanium is employed in the form of titanium metal powder.

19. A process according to claim 17 wherein said titanium is employed in the form of a powdered titanium-cobalt alloy.

20. A process according to claim 17 wherein said titanium is provided by titanium in the interior surface of the reactor vessel.

21. A process according to claim 17 wherein said carbocyclic aromatic compound is toluene and said monoolefinic hydrocarbon is propylene.

22. A process according to claim 17 wherein said carbocyclic aromatic compound is 2-methylnaphthalene.

23. A process according to claim 17 wherein said carbocyclic aromatic compound is selected from o-xylene, p-xylene, or mixtures of o-xylene and p-xylene.

* * * * *